United States Patent
Eifert et al.

(10) Patent No.: US 10,949,607 B2
(45) Date of Patent: Mar. 16, 2021

(54) AUTOMATED DOCUMENT FILTRATION WITH NORMALIZED ANNOTATION FOR DOCUMENT SEARCHING AND ACCESS

(71) Applicant: International Business Machines Corporation, Armonk, NY (US)

(72) Inventors: Cheryl L. Eifert, Watertown, MA (US); Pengwei Yang, Belmont, MA (US); Shang Xue, Cambridge, MA (US)

(73) Assignee: International Business Machines Corporation, Armonk, NY (US)

( * ) Notice: Subject to any disclaimer, the term of this patent is extended or adjusted under 35 U.S.C. 154(b) by 106 days.

(21) Appl. No.: 16/214,923

(22) Filed: Dec. 10, 2018

(65) Prior Publication Data

US 2020/0184006 A1 Jun. 11, 2020

(51) Int. Cl.
*G06F 17/20* (2006.01)
*G06F 40/169* (2020.01)
(Continued)

(52) U.S. Cl.
CPC .......... *G06F 40/169* (2020.01); *G06F 40/157* (2020.01); *G06F 40/194* (2020.01); *G16B 50/00* (2019.02)

(58) Field of Classification Search
CPC ..... G16B 50/00; G06F 40/169; G06F 40/194; G06F 40/157
See application file for complete search history.

(56) References Cited

U.S. PATENT DOCUMENTS 7,130,848 B2   10/2006   Oosta
7,461,006 B2   12/2008   Gogolak
(Continued)

FOREIGN PATENT DOCUMENTS

WO      2016016879 A1      2/2016
WO   WO-2019243486 A1 * 12/2019  ........... G06F 40/232

OTHER PUBLICATIONS

Allot et al., LitVar: a semantic search engine for linking genomic variant data in PubMed and PMC, Nucleic Acids Research, 2018, vol. 46, Web Server Issue, W530-W536 (May 14, 2018) (Year: 2018).*
(Continued)

*Primary Examiner* — Shahid K Khan
(74) *Attorney, Agent, or Firm* — Ryan Lewis; Edell, Shapiro & Finnan, LLC

(57) ABSTRACT

Computer-based methods, systems, and computer readable media for managing documents within a content repository or documents within the document subsets are provided. Variant annotations within the documents may be normalized to a standard nomenclature. A request is processed for the documents including one or more search terms, where the search terms pertain to one or more from a group of genes/gene variants, drugs, and cancer terms. Documents are identified that satisfy the request by comparing the one or more search terms to the normalized annotations and specific sections of the documents, and determining a relevance of a document based on the comparison and a frequency of the one or more search terms in each of the specific sections. The identified documents are ranked in accordance with a priority based on the determined relevance.

20 Claims, 12 Drawing Sheets

(51) Int. Cl.
*G16B 50/00* (2019.01)
*G06F 40/157* (2020.01)
*G06F 40/194* (2020.01)

(56) References Cited

U.S. PATENT DOCUMENTS

| | | | |
|---|---|---|---|
| 8,903,825 | B2 | 12/2014 | Parker et al. |
| 9,483,532 | B1 | 11/2016 | Zhang et al. |
| 9,495,349 | B2 | 11/2016 | Angell et al. |
| 9,690,861 | B2 | 6/2017 | Boloor et al. |
| 10,713,440 | B2 | 7/2020 | Pestian et al. |
| 2001/0034023 | A1 | 10/2001 | Stanton et al. |
| 2003/0177112 | A1* | 9/2003 | Gardner ............... G16B 50/00 |
| 2004/0142325 | A1* | 7/2004 | Mintz .................... A61P 29/00 |
| | | | 435/6.12 |
| 2005/0060305 | A1 | 3/2005 | Hopkins et al. |
| 2007/0112748 | A1 | 5/2007 | Angell et al. |
| 2008/0027913 | A1 | 1/2008 | Chang et al. |
| 2009/0019032 | A1 | 1/2009 | Bundschus et al. |
| 2011/0119212 | A1 | 5/2011 | De Bruin et al. |
| 2012/0116795 | A1 | 5/2012 | Ledley |
| 2013/0013603 | A1 | 1/2013 | Parker et al. |
| 2013/0091126 | A1 | 4/2013 | Krishnaswami et al. |
| 2013/0096946 | A1 | 4/2013 | Shah et al. |
| 2013/0144887 | A1 | 6/2013 | Chen et al. |
| 2014/0280086 | A1 | 9/2014 | Bouadjenek et al. |
| 2015/0088888 | A1 | 3/2015 | Brennan et al. |
| 2016/0019299 | A1 | 1/2016 | Boloor et al. |
| 2016/0048564 | A1 | 2/2016 | Bassett, Jr. et al. |
| 2016/0210426 | A1 | 7/2016 | Robinson et al. |
| 2016/0232321 | A1 | 8/2016 | Silverman |
| 2017/0255743 | A1 | 9/2017 | Torkamani |
| 2018/0081859 | A1 | 3/2018 | Snider et al. |
| 2018/0137249 | A1 | 5/2018 | Eggebraaten et al. |
| 2018/0137433 | A1 | 5/2018 | Devarakonda et al. |
| 2018/0211174 | A1 | 7/2018 | Allen et al. |
| 2018/0373844 | A1 | 12/2018 | Ferrandez-Escamez et al. |
| 2019/0034593 | A1 | 1/2019 | Bouman |
| 2019/0042563 | A1 | 2/2019 | Pestian et al. |
| 2019/0130073 | A1 | 5/2019 | Sun et al. |
| 2020/0175020 | A1 | 6/2020 | Eifert et al. |
| 2020/0175021 | A1 | 6/2020 | Eifert et al. |
| 2020/0218719 | A1 | 7/2020 | Eifert et al. |
| 2020/0226164 | A1 | 7/2020 | Eifert et al. |
| 2020/0227176 | A1 | 7/2020 | Eifert et al. |

OTHER PUBLICATIONS

Wei et al., tmVar: a text mining approach for extracting sequence variants in biomedical literature, Bioinformatics, vol. 29, No. 11 (Year: 2013).*
Wei et al., "tmVar 2.0: integrating genomic variant information from literature with dbSNP and ClinVar for precision medicine." doi: 10.1093/bioinformatics/btx541. Bioinformatics. Jan. 1, 2018;34(1): pp. 80-87.
Allot et al., "LitVar: A Semantic Search Engine for Linking Genomic Variant Data in PubMed and PMC." Nucleic Acids Research, vol. 46. Web Server issue (2018): W530-W536. PMC. Web., Aug. 15, 2018, 7 pages.
Wei et al., "GNormPlus: An Integrative Approach for Tagging Genes, Gene Families, and Protein Domains." BioMed Res Int 2015, vol. 2015, Article ID 918710, http://dx.doi.org/10.1155/2015/918710, Sep. 2015, 7 pages.
Seva et al., "Track 4: Mining protein interactions and mutations for precision medicine (PM)," BioCreative, 2017. www.biocreative.org/media/store/files/2018/BC6_track4_13.pdf, 5 pages.
Yepes et al., "Mutation extraction tools can be combined for robust recognition of genetic variants in the literature" [version 2; referees: 2 approved, 1 approved with reservations]. F1000Research 2014, 3:18 (doi: 10.12688/f1000research.3-18.v2), Nov. 2017, pp. 1-27.
Ravikumar et al., "Text Mining Facilitates Database Curation—Extraction of Mutation-Disease Associations from Bio-Medical Literature." BMC Bioinformatics, 16 (2015): 185, pp. 1-15.
Asma et al., "DiMeX: A Text Mining System for Mutation-Disease Association Extraction." PLoS ONE, 11(4): e0152725, 2016, 26 pages.
LexisNexus, "Developing a Search with LexistNexis." © 2014 LexisNexis. NBI01326-0 0414, https://www.lexisnexis.com/bis-user-information/docs/developingasearch.pdf, pp. 1-17.
U.S. National Library of Medicine, "Search Strategy Used to Create the Systematic Reviews Subset on PubMed," 2018, https://www.nlm.nih.gov/bsd/pubmed_subsets/sysreviews_strategy.html, Accessed Aug. 17, 2018, 2 pages.
U.S. National Library of Medicine, "PubMed Help," Bookshelf ID: NBK3827, 2018, https://www.ncbi.nlm.nih.gov/books/NBK3827, National Center for Biotechnology Information, Accessed Aug. 17, 2018, 125 pages.
Weng et al., "Medical Subdomain Classification of Clinical Notes Using a Machine Learning-Based Natural Language Processing Approach." BMC Medical Informatics and Decision Making 17 (2017): 155. PMC. Web., Aug. 16, 2018, pp. 1-13.
Kafkas et al., "Section Level Search Functionality in Europe PMC." Journal of Biomedical Semantics 6 (2015): 7. PMC. Web. Aug. 16, 2018, pp. 1-5.
Hofmann et al., "The impact of document structure on keyphrase extraction." In Proceedings of the 18th ACM conference on Information and knowledge management (CIKM '09). ACM, New York, NY, USA, 2009, pp. 1725-1728.
Xu et al., "A semi-supervised approach to extract pharmacogenomics-specific drug—gene pairs from biomedical literature for personalized medicine," Journal of Biomedical Informatics, vol. 46, Issue 4, 2013, pp. 585-593.
Lee et al., "Deep learning of mutation-gene-drug relations from the literature." BMC Bioinformatics (2018), 19:21. Published: Jan. 25, 2018, pp. 1-13.
Huang et al., "Predicting drug efficacy based on the integrated breast cancer pathway model," 2011 IEEE International Workshop on Genomic Signal Processing and Statistics (GENSIPS), San Antonio, TX, Dec. 2011, pp. 42-45.
Artemov et al., "A Method for Predicting Target Drug Efficiency in Cancer Based on the Analysis of Signaling Pathway Activation." Oncotarget, vol. 6, No. 30, www.impactjournals.com/oncotarget/, Aug. 2015, pp. 29347-29356.
Allahyari et al., "A Brief Survey of Text Mining: Classification, Clustering and Extraction Techniques", https://arxiv.org/pdf/1707.02919.pdf, Cornell Library University, arXiv:1707.02919v2 [cs.CL], Jul. 28, 2017, 13 pages.
Clematide et al., "Ranking Relations between Diseases, Drugs and Genes for a Curation Task", Journal of Biomedical Semantics, https://jbiomedsem.biomedcentral.com/articles/10.1186/2041-1480-3-S3-S5, Oct. 5, 2012, pp. 1-22.
Wu et al.; "Ranking Gene-Drug Relationships in Biomedical Literature using Latent Dirichlet Allocation", NCBI, https://www.ncbi.nlm.nih.gov/pmc/articles/PMC4095990/; Pac Symp Biocomput, Author manuscript, Jul. 14, 2014, pp. 1-15.
Chen et al., "IBM Watson: How Cognitive Computing Can Be Applied to Big Data Challenges in Life Sciences Research". Clinical Therapeutics, 2016, 38(4):688-701. doi: 10.1016/j.clinthera.2015.12.001. Epub Apr. 21, 2016, pp. 688-701.
NCBI, "PubMed", US National Library of Medicine National Institute of Health, 2018; https://www.ncbi.nlm.nih.gov/pubmed/ (accessed Nov. 30, 2018), 2 pages.
U.S. National Library of Medicine, "MEDLINE/PubMed Resources Guide", 2018, https://www.nlm.nih.gov/bsd/pmresources.html (accessed Nov. 30, 2018), 7 pages.
List of IBM Patents or Patent Applications Treated As Related dated Mar. 26, 2019.
Tamborero et al., "Cancer Genome Interpreter Annotates The Biological and Clinical Relevance of Tumor Alterations" Genome Medicine (Mar. 28, 2018) 10(25): 8 pages, doi: https://doi.org/10.1101/140475.

* cited by examiner

AUTOMATED DOCUMENT FILTRATION WITH NORMALIZED ANNOTATION FOR DOCUMENT SEARCHING AND ACCESS

1. TECHNICAL FIELD

Present invention embodiments relate to automated document filtration and access, and more specifically, to normalizing annotations and annotating documents in order to intelligently access specific combinations of information.

2. DISCUSSION OF THE RELATED ART

Databases and article repositories often contain a large corpus of documents of varying types of information. For example, a user may search NCBI's PubMed® database for different types of peer-reviewed scientific and clinical documents containing information about genomic alterations associated with tumor development and progression.

Many of these types of genomic alterations can be routinely detected in tumor samples by standard next-generation sequencing technologies, including gene/protein mutations, insertions/deletions, copy number alterations, chromosomal rearrangements, and viral integrations. However, there is not a universal standard for how these alterations should be annotated, and therefore, a single variant may be represented in many different manners within a corpus of documents.

Current approaches to normalizing variants are limited in that such approaches are not able to extract some types of variations, such as complex or structural variations, and are simplistic. Additionally, given that a variant may be represented in a variety of different forms in a document, current search technologies may identify only a subset of available information corresponding to the gene variant when the search does not contain all available forms. Accordingly, information provided about a gene variant from a search is often incomplete and important data and other relationships may be missed by a researcher.

SUMMARY

According to embodiments of the present invention, methods, systems and computer readable media are provided for normalizing annotations for 'omics data (e.g., genomic, transcriptomic, proteomic, etc.), in order to facilitate intelligent access of specific combinations of information in a content repository. Rules-based approaches may be used for normalizing annotations and annotating documents within the content repository.

Documents may be classified within the content repository into one of a functional category and a clinical category. Variant annotations within the documents may be normalized to a standard nomenclature. A request is processed for the documents including one or more search terms, where the search terms pertain to one or more from a group of genes/gene variants, drugs, and cancer terms. Documents are identified that satisfy the request by comparing the one or more search terms to the normalized annotations and specific sections of the documents, and determining a relevance of a document based on the comparison and a frequency of the one or more search terms in each of the specific sections. The identified documents are ranked in accordance with a priority based on the determined relevance.

In a preferred embodiment, variant annotations are normalized by extracting gene variants within a document, and by associating each extracted gene variant with a unique identifier corresponding to that gene variant. Associating the variant with a unique identifier allows a standard nomenclature to be generated for each variant, which allows identification of the variant across a corpus of documents. Optionally, for each gene variant, a corresponding gene may be extracted and associated with the corresponding gene. By linking the gene variant to its respective gene, a map may be constructed of the relationship between a gene and its various variants, including locations of the variants relative to the gene.

In an advantageous embodiment, multiple forms of the gene variant are identified, where the forms are selected from the group consisting of a DNA sequence, a RNA sequence, an amino acid sequence, or a phrase containing a reference to the variant, as well as other possible forms comprising information pertaining to the gene variant. By extracting various forms, the quality and completeness of the information provided about the gene variant during a search may be improved, as more forms of the variant are identified during the search.

Preferably, a dictionary for each gene variant is generated, where the dictionary comprises the multiple forms of the gene variant and the corresponding unique identifier for that gene variant. This facilitates detection of the variant, e.g., using a rules-based model, using the information contained in the dictionary.

Optionally, the search term(s) may include a gene or gene variant and specific sections of a document may be used to rank the document, e.g., such as the results section of respective documents. This allows different sections of a document to be differentially weighted, as the presence of a variant in the results section is typically a marker of relevance for the variant, while the presence of a variant in the introduction may indicate limited relevance. This approach may improve ranking of relevant articles.

Advantageously, new relationships may be identified between the entities based on analyzing the normalized variant annotations. The new relationships may provide additional therapeutic targets for physicians, may lead to improved and diverse treatment option for patients, and potentially allow improvements in personalized medicine, as new relationships may be associated with the specific variants identified in a patient. For example, the corpus of documents may be searched for a specific variant present in a patient, and the results of the search used to tailor therapeutic options (e.g., selection of a drug) to that patient.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components.

DETAILED DESCRIPTION

Methods, systems, and computer readable media are provided to manage documents, including normalizing variant annotations of 'omic information and annotating documents. The annotated documents, which indicate which genes and gene variants as well as cancer-types, drugs, and other types of information are provided within a document, may reside in a database.

Using a user interface, a user may search for documents in a content repository based upon document categories (e.g., clinical, functional, case report, review article or meeting & proceeding abstract, etc.), as well as normalized terms for gene names, gene variant/mutation names, drugs, cancer types/cancer names, or any combination of the preceding as well as synonyms thereof. Present techniques identify all or nearly all forms of gene/protein mutations as well as other types of genomic alterations, including insertions/deletions, copy number alterations, chromosomal rearrangements, and viral integrations. A rules-based module may be used to extract and associate gene and variant information, as part of normalizing to a standard nomenclature. In an aspect, the results section of an article may be evaluated to identify and annotate such gene and gene variants.

Documents that satisfy the search request may be identified by comparing the one or more search terms to the normalized annotations. The documents may be scored based on a measure of relevance of a document based on the comparison and a frequency of the one or more search terms in specific sections of the documents. Results may be provided as a ranked list of documents based upon a priority score.

Figure 1:
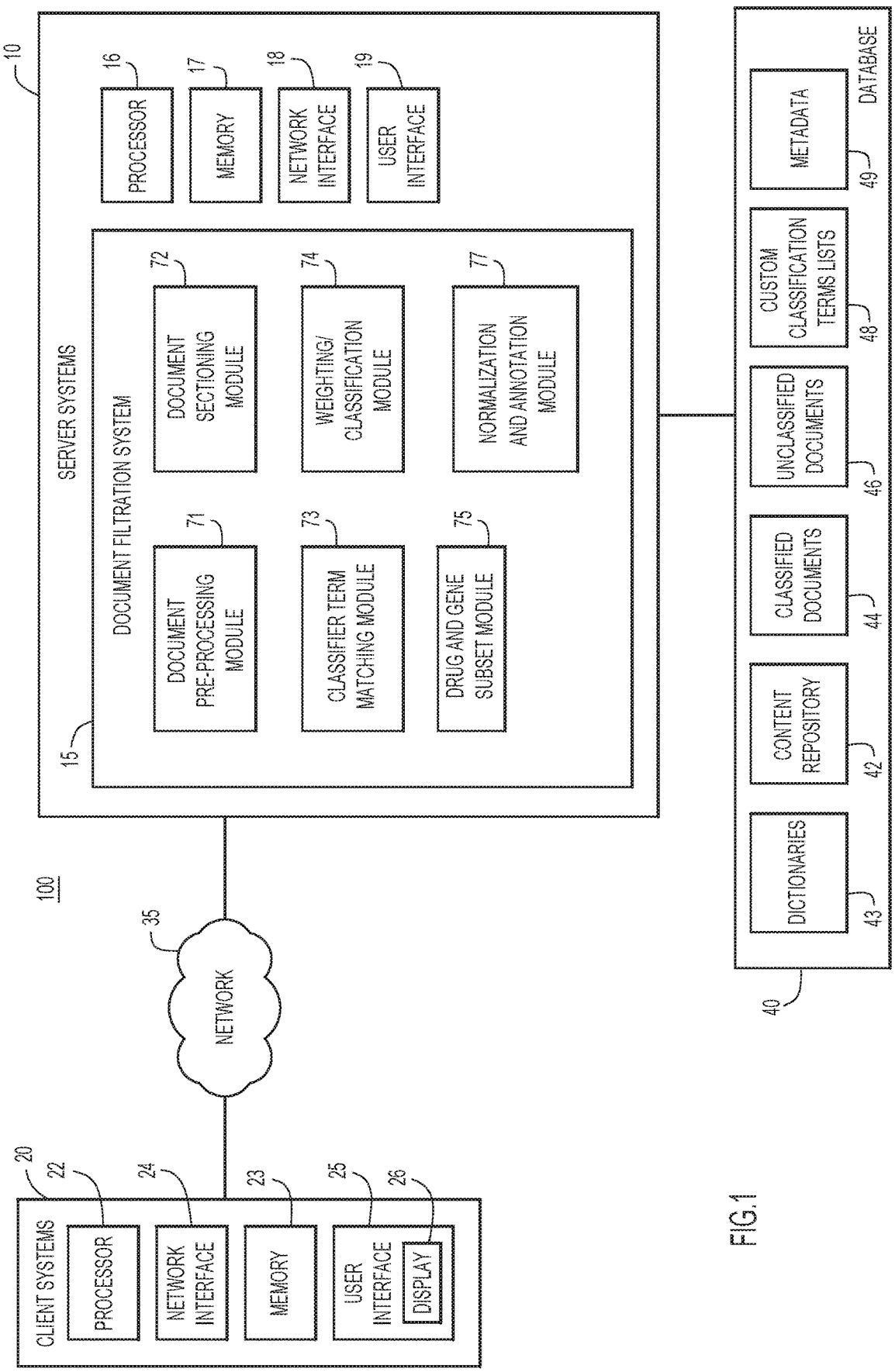
FIG. 1 is a block diagram of an example computing environment for the document filtration and normalized annotation system, according to embodiments of the present disclosure.

An example environment for use with present invention embodiments is illustrated in FIG. 1. Specifically, the environment includes one or more server systems 10, and one or more client or end-user systems 20. Server systems 10 and client systems 20 may be remote from each other and communicate over a network 35. The network may be implemented by any number of any suitable communications media (e.g., wide area network (WAN), local area network (LAN), Internet, Intranet, etc.). Alternatively, server systems 10 and client systems 20 may be local to each other, and communicate via any appropriate local communication medium (e.g., local area network (LAN), hardwire, wireless link, Intranet, etc.).

Client systems 20 enable users to access documents (e.g., functional documents, clinical documents, case studies, review articles, or meeting and proceeding abstracts, etc.) that have been annotated with genomic and proteomic information (or other types of 'omic information) from server systems 10 for analysis and review. The server system may include a document filtration system 15 to classify and annotate documents using a standard nomenclature in order to select and prioritize relevant information.

A database system 40 may store various information for the filtration (e.g., content repository 42, classified documents 44, unclassified documents 46, custom classification terms lists 48, metadata 49, dictionaries 43, etc.). The database system may be implemented by any conventional or other database or storage unit, may be local to or remote from server systems 10 and client systems 20, and may communicate via any appropriate communication medium (e.g., local area network (LAN), wide area network (WAN), Internet, hardwire, wireless link, Intranet, etc.). The client systems may present a graphical user (e.g., GUI, etc.) or other interface (e.g., command line prompts, menu screens, etc.) to solicit information from users pertaining to the desired documents and filtration, and may provide reports including filtration results (e.g., percentage of documents classified into a respective category, percentage of documents not classified into a respective category, number of terms of a custom classification terms list found in a document, frequency of search terms in documents scored according to a priority score, normalized terms, etc.).

Server systems 10 and client systems 20 may be implemented by any conventional or other computer systems preferably equipped with a display or monitor 26, a base (e.g., including at least one processor 16, 22 one or more memories 17, 23 and/or internal or external network interfaces or communications devices 18, 24 (e.g., modem, network cards, etc.)), optional input devices (e.g., a keyboard, mouse or other input device) and/or user interface 19, 25 and any commercially available and custom software (e.g., server/communications software, document filtration system 15, browser/interface software, etc.).

Alternatively, one or more client systems 20 may analyze documents to determine document classification and normalized annotation when operating as a stand-alone unit. In a stand-alone mode of operation, the client system stores or has access to the content repository 42 and custom classification terms lists 48 as well as the document filtration system 15. The graphical user (e.g., GUI, etc.) or other user interface (e.g., command line prompts, menu screens, etc.) may solicit information from a corresponding user pertaining to the document filtration, and may provide reports including search results and document ranking (e.g., percentage of documents classified into a respective category, percentage of documents not classified into a respective category, number of terms of a custom classification terms list found in a document, frequency of search terms in documents scored according to a priority score, normalized terms, etc.).

Document filtration system 15 may include one or more modules or units to perform the various functions of present invention embodiments described herein. The various modules (e.g., document pre-processing module 71, document sectioning module 72, classifier term matching module 73, weighting/classification module 74, drug and gene subset module 75, normalization and annotation module 77, etc.) may be implemented by any combination of any quantity of software and/or hardware modules or units, and may reside within memory 17, 23 of the server and/or client systems for execution by processor 16, 22.

The document pre-processing module 71 may render the documents readable by a machine reader. In some aspects, optical character recognition may be used to recognize text in a document, to render the text readable and searchable. Additionally, text in tables, images, image captions, or lists may also be rendered machine readable. This processing ensures that images of documents, e.g., scanned PDFs, are included in the analysis.

The drug and gene subset module 75 filters content (documents) of the content repository 42 to generate drug subsets and gene subsets of documents. In some cases, a list of drugs or genes may be obtained, for example, from dictionaries generated by normalization and annotation module 77, and used to filter the content of the content repository. For example, normalization and annotation module 77 may generate genomic and proteomic dictionaries, which may be used to link variants to particular genes.

For filtering, if a drug name is found in a document, that document is added to the document subset of drugs. If a gene name is found in a document, that document is added to the document subset of genes.

In some aspects, the documents may be preprocessed using the document preprocessing module 71 prior to filtration by the drug and gene subset module 75. The documents may be provided to the document sectioning module for further processing and analysis. Similar operations may be performed for other entities including gene name synonyms, gene variant name synonyms, drug name synonyms, and cancer-type name synonyms, etc.

The document sectioning module 72 may be used to identify sections of machine readable documents. In some aspects, a document section may identified by an appropriate header. For example, the header "abstract" may indicate the presence of an abstract. The header "introduction" or "background" may indicate the presence of a section describing the current state of the art and/or background to help the reader better understand the context and rationale of the current study. The header "material and methods" may indicate an experimental section that describes the materials and methods and experimental protocols used during the course of experiments. The header "results" may indicate the presence of a results section showing data generated from the experiments. The header "discussion" may indicate the presence of a discussion section which interprets the experimental results. The header "conclusion" may indicate a summary of the experimental results of the document and future areas of investigation.

In some aspects, a section labeled with a header may be further divided into subsections having sub-headings. For example, the abstract may additional contain sub-headers such as "objective", "methods", "results", and "conclusion". In some aspects, subsections of specific subheadings may be targeted to analyze content for specific custom classification terms.

Normalization and annotation module 77 identifies various forms of 'omic information (e.g., gene or gene variant information) that may be present within a corpus of documents. By generating or utilizing an identification tag for the type of information (e.g., a specific genetic variant), the system may map all identified information corresponding to the genetic variant to the identification tag. For example, a DNA, RNA, or protein sequence corresponding to the same molecule may be present in various forms within the corpus, and by mapping each form to the identification tag, information may be aggregated about the variant.

The classifier term matching module 73 may search specific sections of each document for terms in a custom classification terms list 48 or in a dictionary 43. For example, a clinical classification term list may contain single terms or phrases that may be used to identify the document as a clinical document. As another example, a functional classification term list may contain single terms or phrases that may be used to identify the document as a functional document. Similar term lists may be provided for review articles, conference proceedings and abstracts, and case studies. In another example, dictionaries may be used by the classifier term matching module 73 to identify genes and variants in documents of the content repository.

In some aspects, both functional and clinical information may be needed to determine the significance of a given biologic relationship. Functional information provides evidence regarding a gene's and/or gene variant's function, while clinical information provides evidence regarding a patient's response to treatment with a targeted therapy (clinical studies). For instance, the materials and methods section may be searched with custom-designed "functional query terms" to identify and classify functional articles. The abstract may be searched with custom-designed "clinical query terms" to identify and classify clinical articles. In other aspects, the results section may be searched for dictionary terms, which may include multiple forms of the gene variant and the corresponding unique identifier for that gene variant.

The weighting/classification module 74 may classify different documents within the content repository and documents within document subsets into different categories. In some aspects, weighting scores may be used to classify documents as functional or clinical documents. Based on the number of terms or phrases identified in the specific section(s) of the document, a weighting score may be determined (see, FIG. 3). If the weighting score is above a classification threshold value, then the document may be classified into a respective category. Documents may be ranked for presentation to the user based upon the number of times a unique classification term appears in the methods section (for functional articles) or in the abstract section (for clinical articles). The weighting classification module 74 may also classify documents into respective categories (e.g., case study, review article, or conference proceedings and abstract) based on article type tags and/or weighting scores.

In some aspects, once classified, the documents may be stored in designated locations within database 40 (e.g., within classified documents 44), such that functional documents are located in a first directory, clinical documents are located in a second directory, and so forth. Alternatively, documents may be maintained in the same location within the content repository, but associated with metadata 49 that indicates whether the document is classified and the respective category that the document has been classified into.

Documents that the system is not able to classify may be stored in unclassified documents 46. In some aspects, these documents may be moved into a corresponding directory for unclassified documents. Alternatively, documents may be maintained in the same location within the content repository, but associated with metadata 49 that indicates that the documents are unclassified. These documents may be subject to manual review.

FIGS. 2A-2E show various flow charts for classifying documents or document subsets into respective categories. Different types of documents (e.g., scientific publications and clinical articles, review articles, case reports, or meeting/proceeding abstracts, etc.) have certain physical publishing layout requirements including providing various types of data in discrete sections of the document, typically in a predefined order. Sections of the document may also be defined by the publishing requirements, and may include the title, abstract, introduction, materials and methods, analysis/results, and discussion/conclusion sections. These documents may reside in a content repository, where the documents are not classified into a category.

According to present invention embodiments, the documents are rendered machine readable, so that the headings and corresponding text can be processed by the filtration system 15. Each section may contain specific types of information. Accordingly, limiting the search for custom classification terms to particular sections ensures that the documents are classified correctly.

A rules-based module may be used to search in specific sections of a document to classify the type of document (e.g., into a functional or clinical or other category). The sectioned documents can be searched, for example, for user defined custom classification terms within the text of specific sections. Based on the search results, the filtration system can classify the documents in the content repository into a respective category. The rules-based filtering system is configured to search in specific sections of a document to ensure the data originated in the current study, rather than being provided as a reference to another document.

Figure 2A:
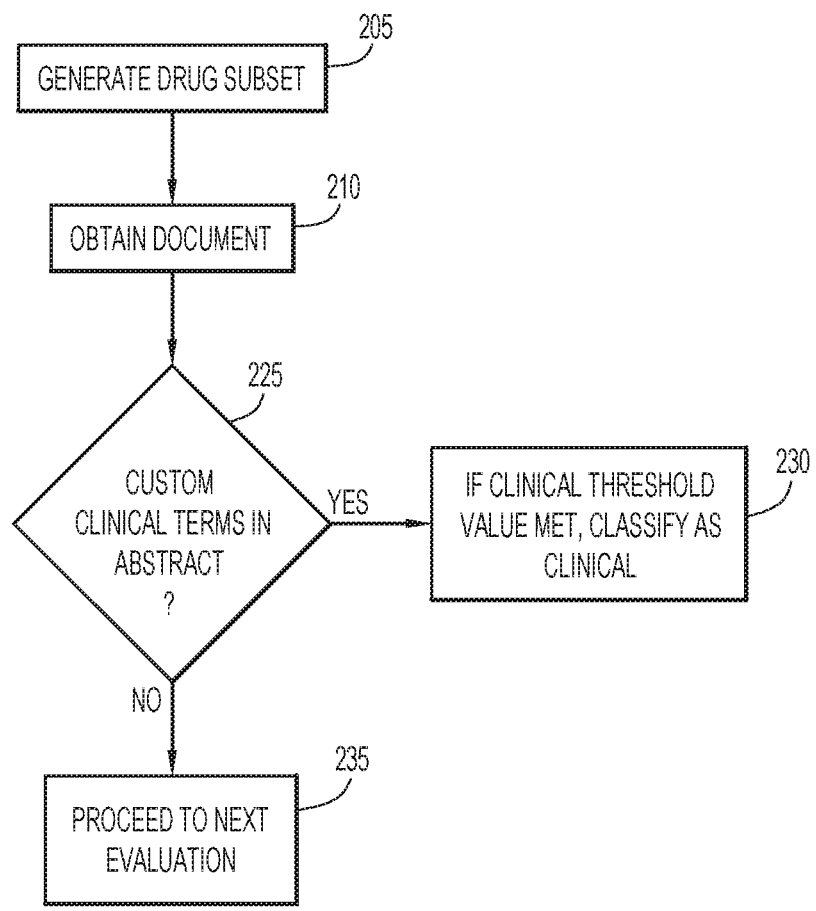
FIGS. 2A-2E are flow diagrams showing classification of a document into a respective category of documents, according to embodiments of the present disclosure.

FIG. 2A shows a flowchart for classifying clinical documents or document subsets. Clinical documents may provide evidence that a specific biologic relationship has important therapeutic ramifications. For example, a clinical document may contain a phrase indicating that overexpression of erbb2 leads to breast cancer or that pertuzumab increases the response rate of HER2-positive breast cancer.

To identify clinical documents, a drug subset of documents is generated at operation 205. A list of drug names may be provided to the drug and gene subset module 75, from the custom classification terms lists 48. Documents of the content repository are filtered using the list of drug names, and if a term (drug name) is found, the document is added to the drug subset of documents. At operation 210, a document is obtained from the content repository. At operation 225, a particular section of the document (e.g., the abstract section) may be searched for custom clinical classification terms and/or phrases. For example, a clinical filter comprising custom classification terms or phrases may be applied to the abstract portions of the documents of the content repository to identify clinical documents. If a threshold condition is met (e.g., the weighting score is greater than a clinical threshold value), at operation 230, the document is classified as clinical. Otherwise, the document may be evaluated for classification into a different category (e.g., functional, case study, review article, conference type and proceedings abstract, etc.) at operation 235.

In some aspects, the document may be moved into a directory associated with clinical documents. Alternatively, the document may remain in the content repository and may be associated with metadata indicating that the document is a clinical document.

Figure 2B:
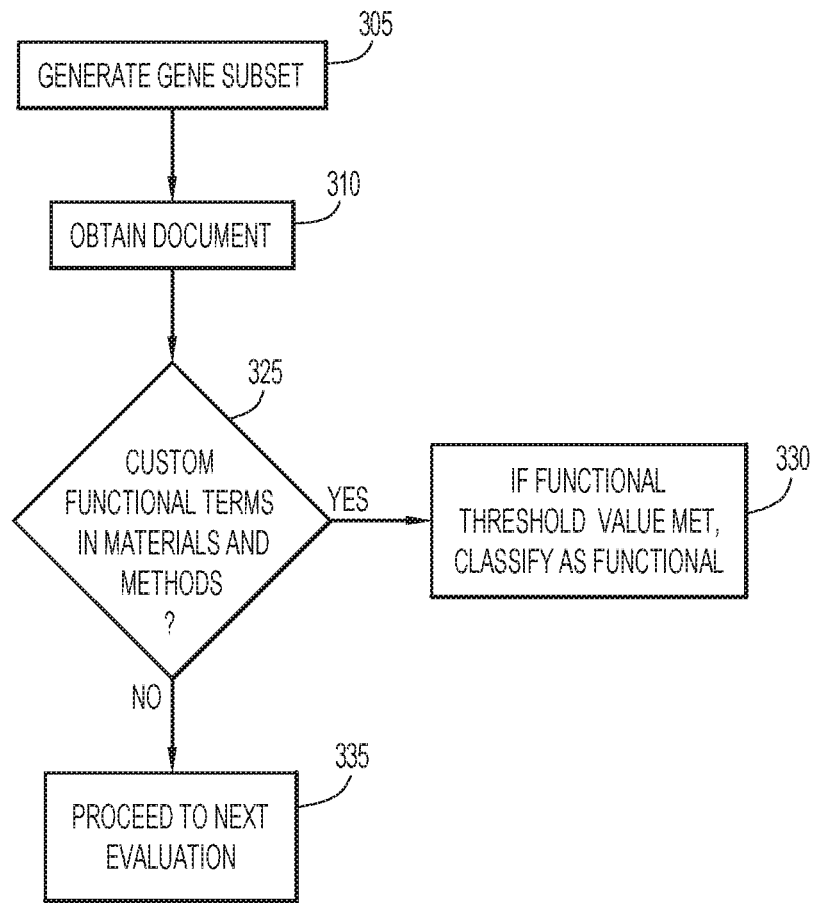

FIG. 2B shows a flowchart for classifying functional documents. Functional documents may provide evidence that a specific genomic alteration is oncogenic or promotes oncogenic properties. For example, a functional document may contain a phrase indicating that HER2 transmembrane domain mutations (V659/G660) stabilize homo- and heterodimerization and are oncogenic drivers. To identify functional documents, the materials and methods section may be searched using a functional filter for custom functional classification terms.

To identify functional documents, a gene subset of documents is generated at operation 305. A list of gene names may be provided to the drug and gene subset module 75, from the custom classification terms lists 48. Documents of the content repository are filtered using the list of gene names, and if a term (gene name) is found, the document is added to the gene subset of documents. At operation 310, a document is obtained from the content repository. At operation 325, a particular section of the document (e.g., the methods and materials section) may be searched for custom functional classification terms and/or phrases. For example, a functional filter comprising custom classification terms or phrases may be applied to the materials and methods portions of the documents of the content repository to identify functional documents. If a threshold condition is met (e.g., the weighting score is greater than a functional threshold value), at operation 330, the document is classified as functional. Otherwise, the document may be evaluated for classification into a different category (e.g., clinical, case study, review article, conference type and proceedings abstract, etc.) at operation 335. In some aspects, the document may be moved into a directory associated with functional documents. Alternatively, the document may remain in the content repository and may be associated with metadata indicating that the document is a functional document.

Figure 2C:
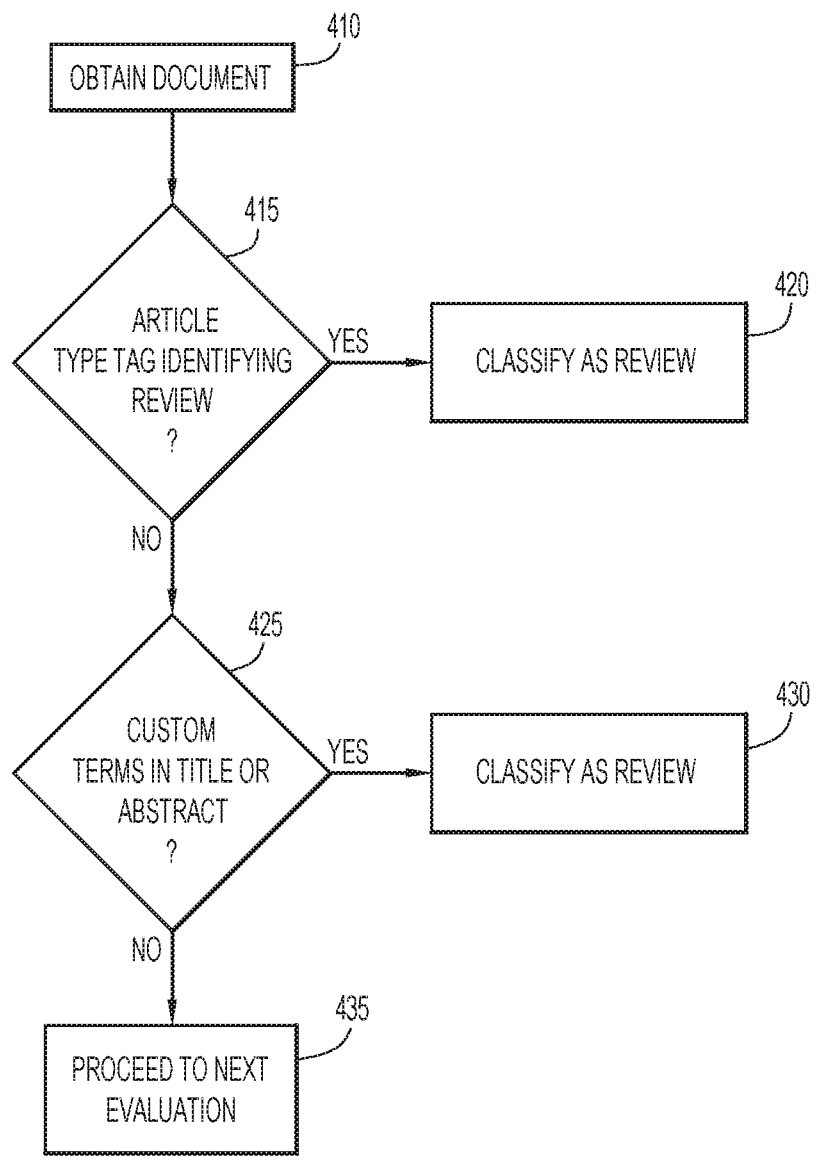

FIG. 2C shows a flowchart for classifying review articles. Review articles may summarize other research documents. For example, a review article may contain references to a plurality of other research documents with a related theme, such as kidney cancer—recent advances and future directions. To identify review articles, the cover page, title, or header may be searched using a review filter for custom review classification terms.

To identify review articles, a document is obtained from the content repository at operation 410. At operation 415, the system determines whether an article type tag is associated with the document that indicates that the document is a review article. In some cases, review articles, conference proceedings and abstracts, and case studies may have an article type tag identifying the type of article. In other cases, clinical and functional studies may not have an article type tag as these categories of documents may contain both types of information in different sections. If such a tag is found, at operation 420, the system classifies the document as a review article. If an article type tag is not found, a particular section of the document (e.g., the title, cover page, headings) may be searched for custom review classification terms and/or phrases at operation 425. For example, a review filter comprising custom classification terms or phrases may be applied to the cover page, title, or headers of the documents of the content repository to identify review articles. For example, review articles generally include the phrase "review article" or equivalent on their front/cover page to indicate that the document is a review article. If a review article term is present, at operation 430, the document is classified as a review article. Otherwise, the document may be evaluated for classification into a different category (e.g., functional, case study, clinical, conference type and proceedings abstract, etc.) at operation 435.

In some aspects, the document may be moved into a directory associated with review articles. Alternatively, the document may remain in the content repository and be associated with metadata indicating that the document is a review article.

Figure 2D:
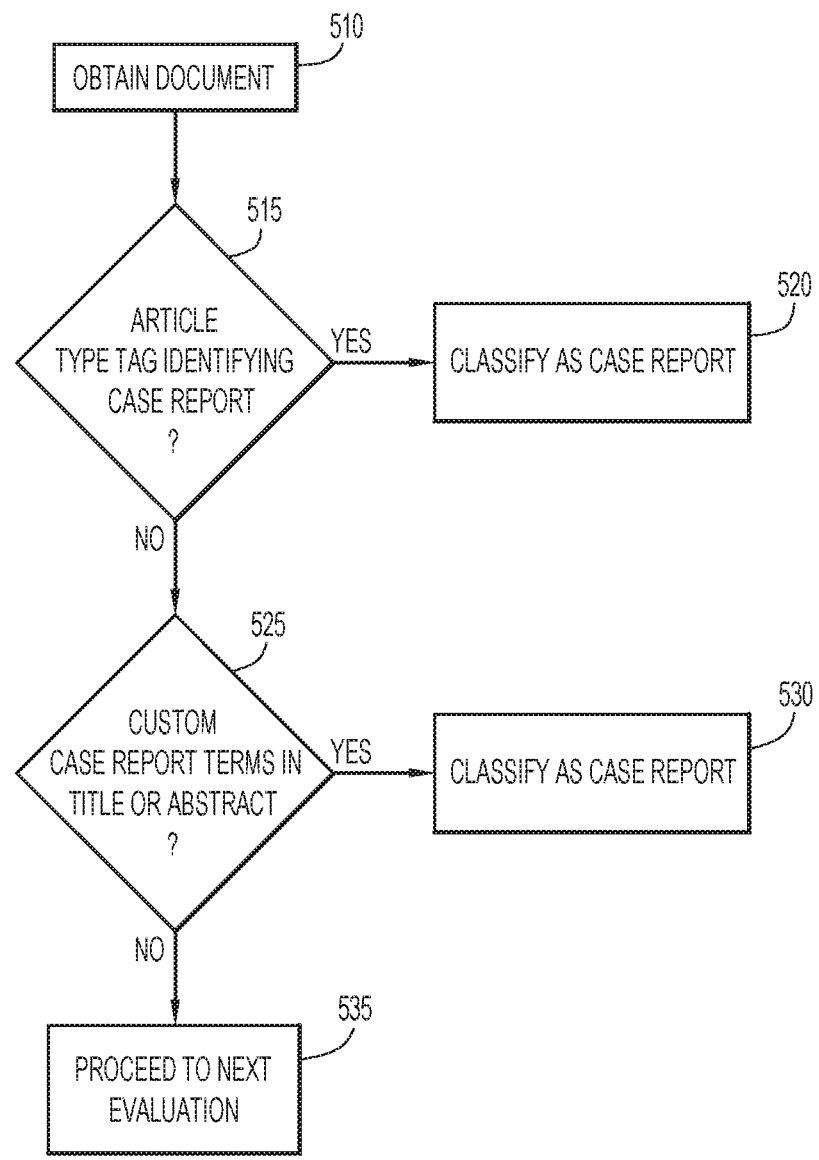

FIG. 2D shows a flowchart for classifying case reports. Case reports may provide information about a single patient, or in some cases, a small number of patients. These documents may not contain a large enough sample size representative of a population, and therefore, may skew data if not properly identified. For example, a case report (or case summary) may discuss a single patient outcome, such as Kartagener syndrome—a case report. To identify case reports, the cover page, title, or header may be searched using a case report filter for custom case report classification terms.

To identify a case report, a document is obtained from the content repository at operation 510. At operation 515, the system determines whether an article type tag is associated with the document that indicates that the document is a case report. An article type tag is typically a numeric identifier associated with documents in a database such as PubMed® or Medline® that identifies the document as a case report. If such a tag is found, at operation 520, the system classifies the document as a case report. If an article type tag is not found, a particular section of the document (e.g., the title, cover page, headings) may be searched for custom review classification terms and/or phrases at operation 525. For example, a case report filter comprising custom classification terms or phrases may be applied to the cover page, title, or headers of the documents of the content repository to identify a case report. For example, a case report generally include the phrase "case report" on their front/cover page to indicate that the document is a case report. If a case report term is present, at operation 530, the document is classified as a case report. Otherwise, the document may be evaluated for classification into a different category (e.g., functional, review article, clinical, conference type and proceedings abstract, etc.) at operation 535.

In some aspects, the document may be moved into a directory associated with case reports. Alternatively, the case report may remain in the content repository and be associated with metadata indicating that the document is a case report.

Figure 2E:
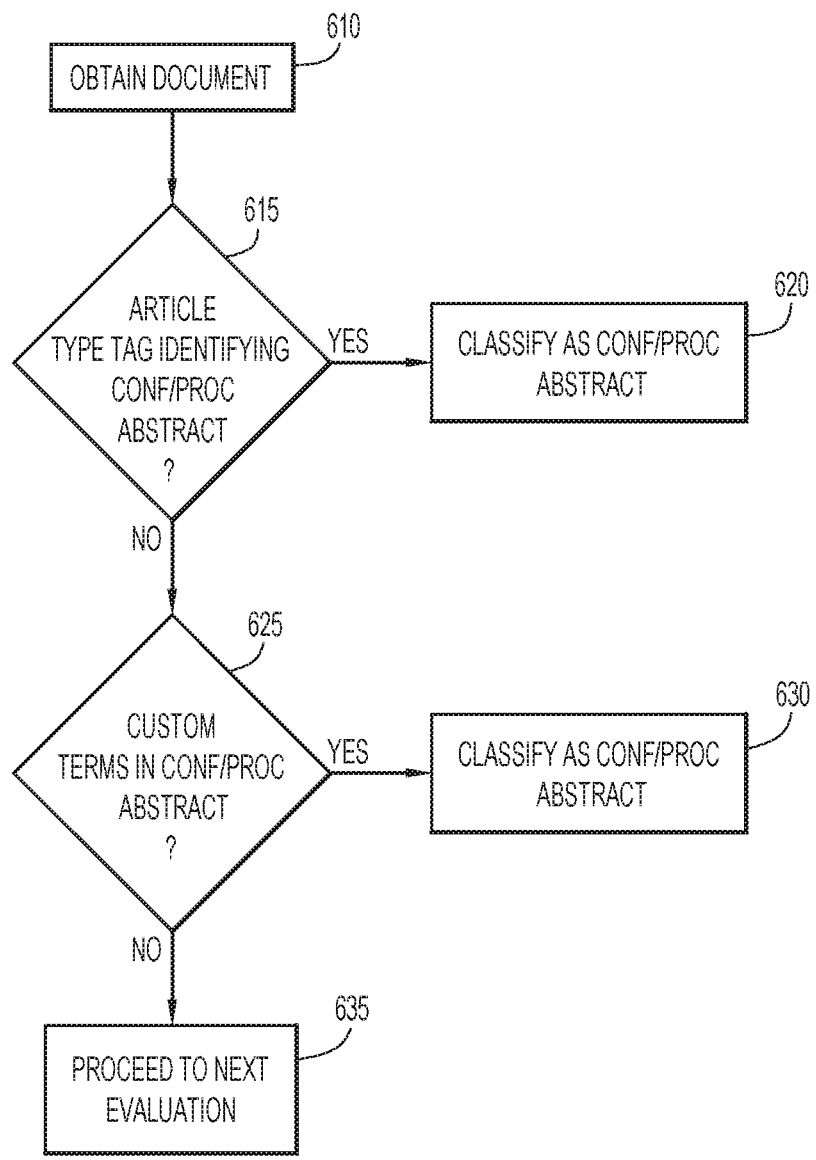

FIG. 2E shows a flowchart for classifying conference proceedings and abstracts. Conference proceedings and abstracts are short documents providing an overview of a presentation or poster from a conference. For example, conference proceedings and abstracts may contain a short summary of a research topic, such as $10^{th}$ Annual Biotechnology Meeting. To identify conference proceedings and abstract documents, the cover page, title, or header may be searched using a conference proceedings and abstract filter for custom conference proceedings and abstract classification terms.

To identify conference proceedings and abstract documents, a document is obtained from the content repository at operation 610. At operation 615, the system determines whether an article type tag is associated with the document that indicates that the document is a conference proceedings and abstract article. If such a tag is found, at operation 620, the system classifies the document as a conference proceedings and abstract document. If an article type tag is not found, a particular section of the document (e.g., the title, cover page, headings, etc.) may be searched for custom conference proceedings and abstract classification terms and/or phrases at operation 625. For example, a conference proceedings and abstract filter comprising custom classification terms or phrases may be applied to the cover page, title, or headers of the documents of the content repository to identify conference proceedings and abstract documents. For example, conference proceedings and abstract documents generally include the phrase "conference proceeding" or abbreviation corresponding to the same on their front/cover page to indicate that the document is a conference proceedings and abstract. If a conference proceedings and abstract term is present, at operation 630, the document is classified as a conference proceedings and abstract. Otherwise, the document may be evaluated for classification into a different category (e.g., functional, review article, clinical, case report, etc.) at operation 635.

In some aspects, the document may be moved into a directory associated with conference proceedings and abstract documents. Alternatively, the document may remain in the content repository and be associated with metadata indicating that the document is a conference proceedings and abstract article.

In some aspects, a document may be classified both as a clinical document and as a functional document. In general, review articles, case reports and meeting/proceeding abstracts will not overlap in regards to classification. Classification may be performed in any evaluation order, such that the document may be evaluated with regard to the order shown in FIG. 2A-2E, or any other suitable order, and have any quantity of classifications.

Once all evaluations have been performed, then the process may terminate. Documents that are not identified, remain unclassified.

Figure 3:
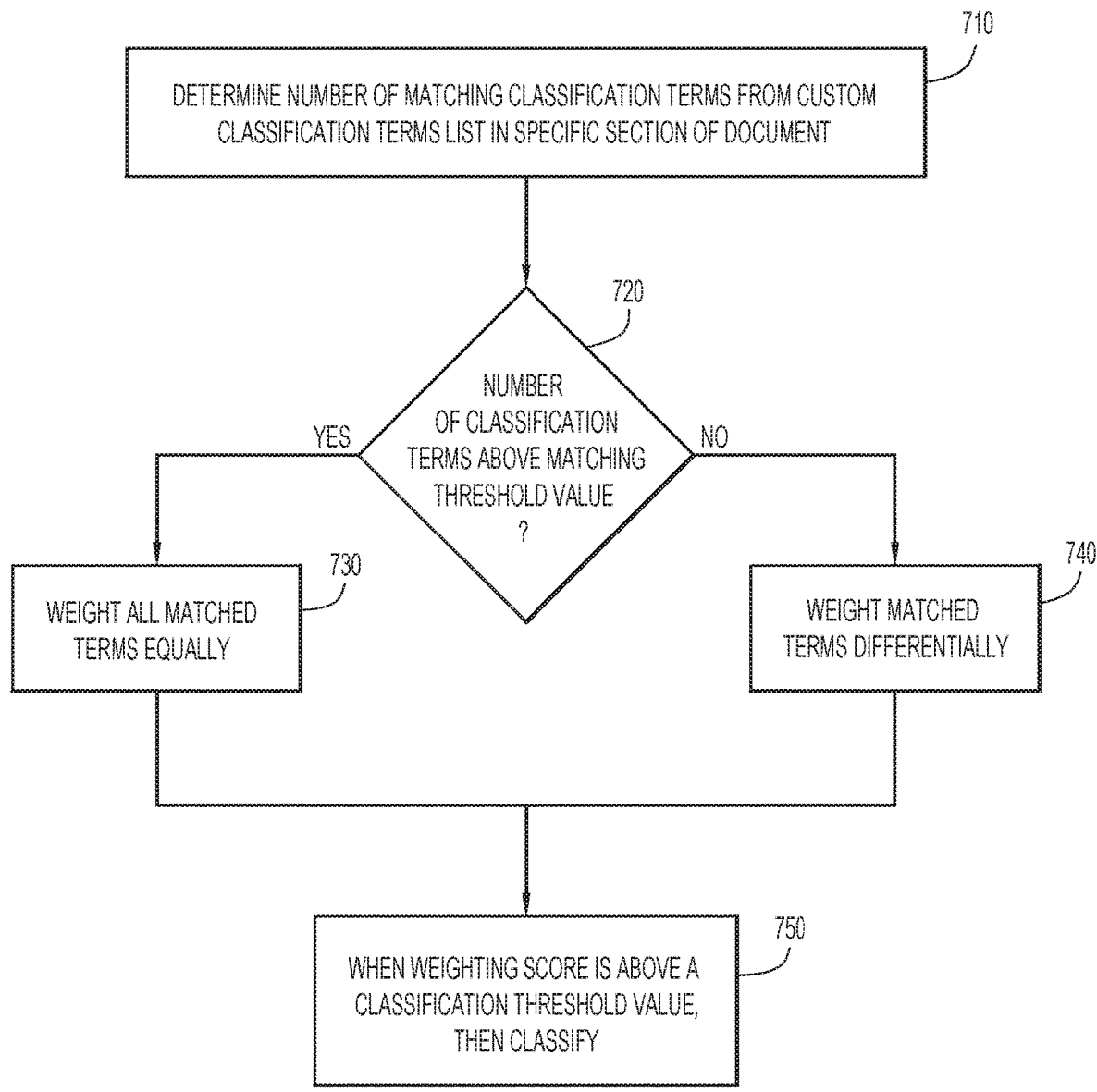
FIG. 3 is a flow diagram showing weighting of matching classification terms from a custom classification terms list for classification of the document, according to embodiments of the present disclosure.

FIG. 3 shows example operations of weighting matched classification terms (e.g., terms from a custom classification terms list that are found in a section of a document) for classification of the document. Custom classification terms may be weighted equally or differentially, as shown in FIG. 3, and results may be aggregated to determine classification of the document.

At operation 710, the number of matching classification terms of a custom classification terms list for a specific section of the document is determined. If the number of unique terms is above a matching threshold value (e.g., seven or more unique terms), all terms are weighted equally, at operation 730. If the weighting score (e.g., a sum of each unique term times a weighting factor of 1) is above a classification threshold value, then the document is classified accordingly at operation 750. If the custom classification terms list is a functional terms list, then the document is classified as a functional document. If the custom classification terms list is a clinical term list, then the document is classified as a clinical document.

If the number of matching classification terms is below a matching threshold value, the matched terms are weighted differentially (e.g., four unique terms may be weighted with a factor of 0.3, five unique terms may be weighted with a factor of 0.6, and six unique terms may be weighted with a factor of 0.8), at operation 740. If the weighting score (e.g., sum of each unique term times a respective weighting factor) is above a classification threshold value, then the document is classified accordingly at operation 750. For example, if too few unique terms are identified, and the weighting score is below a classification threshold value, then the document will not be classified in the respective category.

Figure 4:
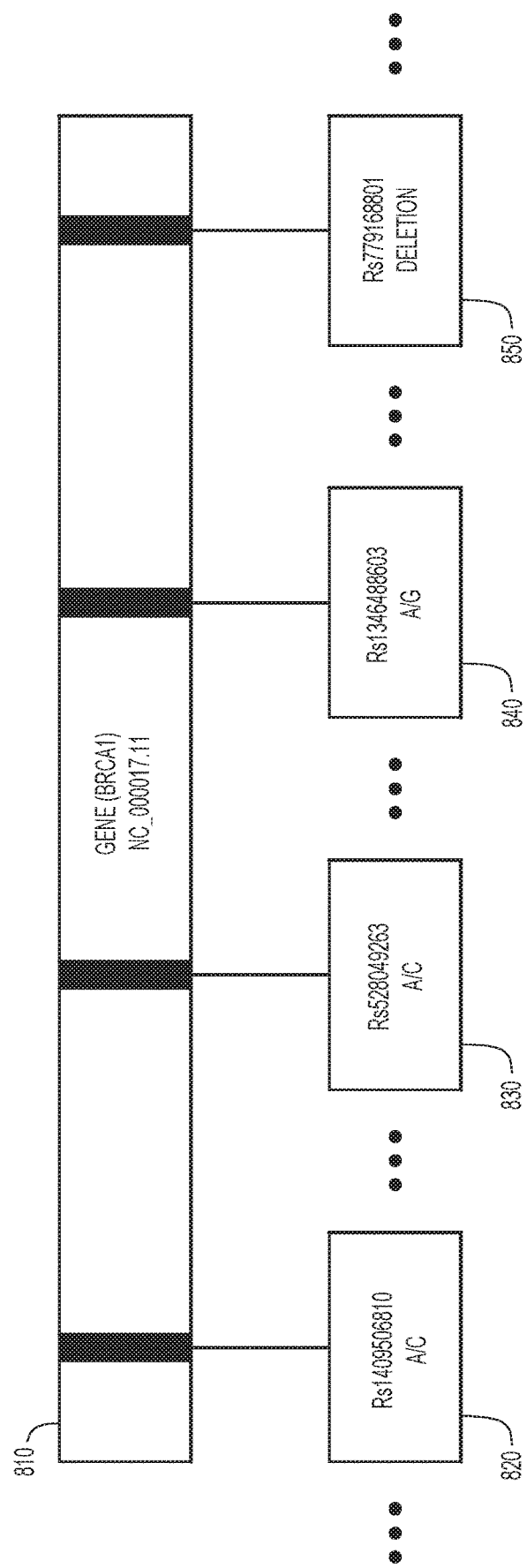
FIG. 4 is an illustration of a gene and examples of known gene variants, according to embodiments of the present disclosure.

FIG. 4 is an example of a gene and corresponding variants. Gene 810 represents an example gene (BRCA1), which has been implicated in the development and progression of breast cancer. An identifier is shown corresponding to this gene (NC_000017.11). As shown in this figure, four different variants of BRCA are provided (many more are known in the art), identified by a corresponding ICEID (e.g., Rs1409506810). The ICEID is a unique identifier which references a particular genetic variant of gene 810. In this case, example variants are variants 820, 830, 840 and 850. Variants 820, 830, and 840 are variants with single mutations (e.g., A to C or A to G), while variant 840 contains a deletion. In this example, each of these variants map to a different region of the gene 810. For a particular gene that is known to be implicated in cancer, such as BRCA1, the present techniques provide information about which variants of a gene, based on information and relationships identified in the literature, respond to particular therapeutics in a specific patient population (e.g., a cohort population).

Figure 5:
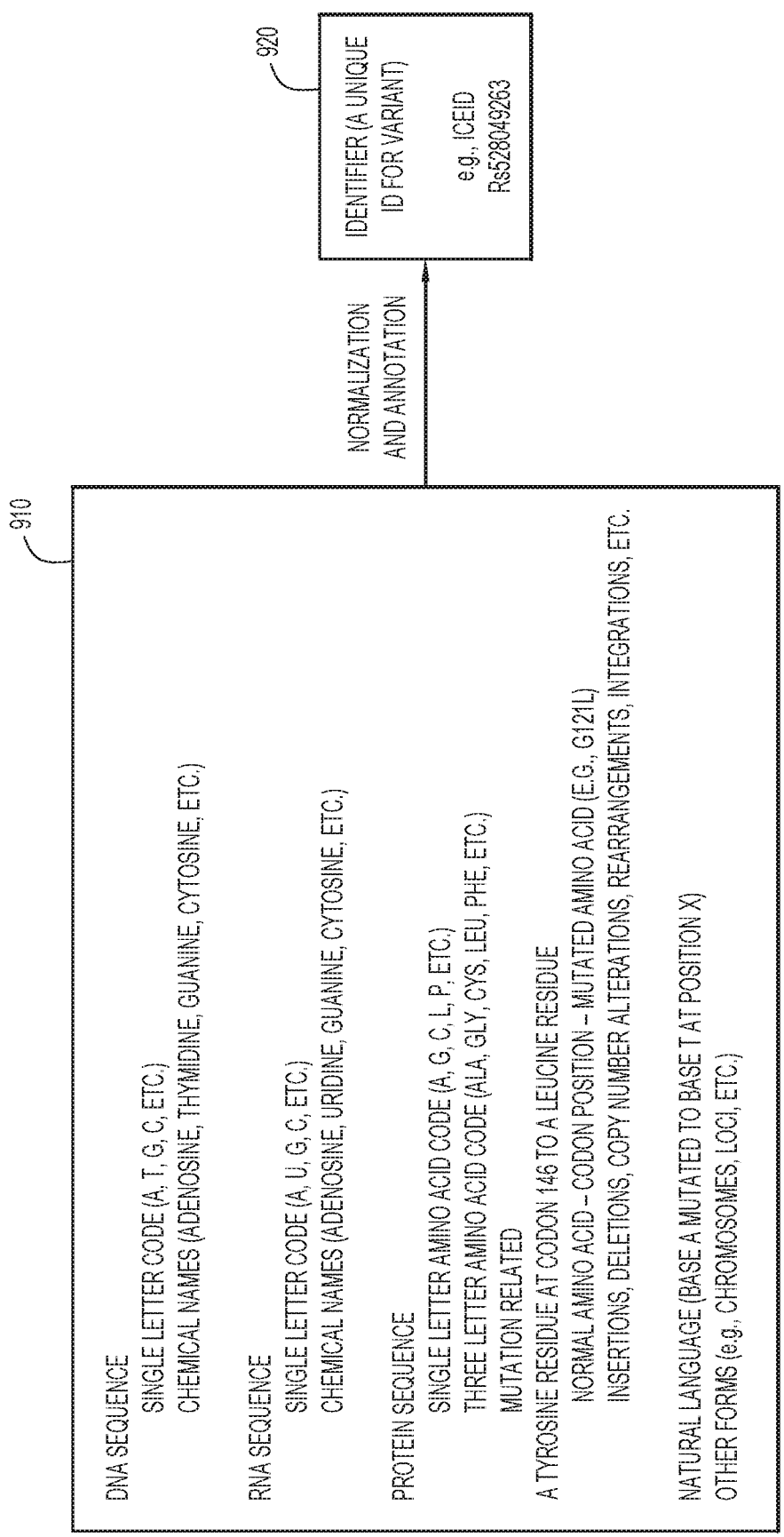
FIG. 5 is a table showing various forms in which variant information may be provided within the corpus, according to embodiments of the present disclosure.

FIG. 5 shows an example of representing variant information in different forms in a corpus of documents. As shown by block 910, a variant may be represented in the literature in a variety of different forms. The same gene mutation may be reported in the literature and databases in many different ways (e.g., nucleotide sequences, protein sequences, three-letter amino-acid-codes, single letter amino-acid codes, different RNA transcripts, language such as "substitution of a tyrosine residue at codon 146 to a leucine residue" in a specific protein, etc.). The normalization and annotation module normalizes variants to a standard nomenclature. For example, the DNA sequence of the variant may be provided, represented by single letter codes or by chemical names. In other examples, the RNA sequence corresponding to the mutation may be provided, represented by a single letter code or chemical names.

In yet another embodiment, a mutation may be represented by an amino acid sequence. In this case, the amino acid representation may be represented as a single letter amino acid code, a three letter amino acid code, or the position of the mutation and type of mutation may be specified (e.g., G121L may indicate that a glycine has been mutated to a leucine at codon 121). As other examples, the mutation may be described in natural language or other forms including insertions, deletions, copy number alterations, chromosomal rearrangements, and viral integrations, etc. on chromosomes, loci of chromosomes, etc.

The normalization and annotation module, which may be a rules-based module, identifies these various forms and converts these forms to a standardized form. For example, the normalization and annotation module may be configured to identify references to a gene variant, including identification of a nucleic acid sequence corresponding to the variant, an identifier from a database or other source corresponding to the variant, a phrase containing a reference to the variant, etc. In some cases, the normalization and annotation module may access a dictionary comprising a list of representations of the gene variant, and may search a document for this information.

In one example, an identifier, which is a unique ID for a variant, may be used as shown in block 920. For example, an ICEID or any other suitable variant may be used. Using these techniques, a corpus of documents may be analyzed for a variant, the variant in all identified forms may be mapped to a single ICEID to represent all identified forms. In some cases, the variants may be mapped to a gene, allowing a global view of all information pertaining to a gene and its variants. Any suitable identifier may be used, as the present techniques are not limited to ICEIDs. For example, any unique identifier corresponding to a variant in a database may be used. In some cases, the variants may be rare. In other cases, the variants may be commonly found across a population of individuals (e.g., SNPs). Additional details about the rules-based module are provided below.

Figure 6:
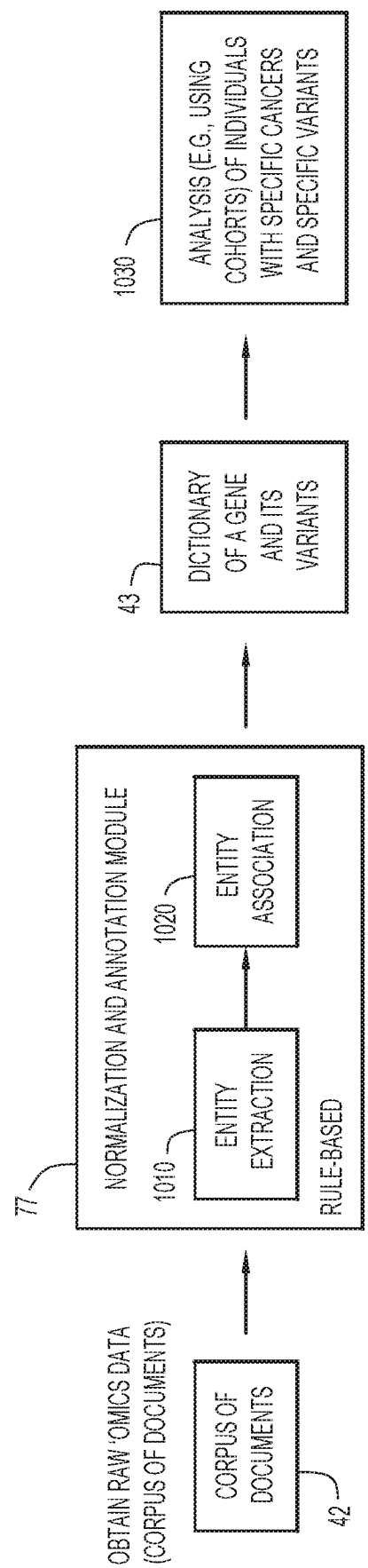
FIG. 6 is an example flowchart showing operations of the normalization and annotation module, according to embodiments of the present disclosure.

FIG. 6 shows example operations of the normalization and annotation module 77. In this example, a corpus of documents 42 containing variants (e.g., as part of various 'omics data) may be provided to the filtration system 15, which comprises the normalization and annotation module 77. The normalization and annotation module 77 may perform entity extraction at operation 1010, in which gene variants and genes are extracted, and may also perform entity association at operation 1020, in which variants are associated with a particular gene. An entity may represent, but is not limited to, a genetic variant, gene, drug, cancer-type, etc. In some aspects, the normalization and annotation module 77 identifies and extracts entities (e.g., data corresponding to gene variants) using rules-based (pattern matching, syntactic, grammatical, etc.) techniques. The information may be normalized (e.g., mapped to a unique identifier), as part of the process of generating a dictionary 43 (e.g., a gene variant dictionary, including various forms of a specific gene variant, represented as an ICEID or other suitable ID).

In some aspects, new associations may be identified from generating a dictionary (e.g., variants present within a document (e.g., present within the same sentence, or within a similar context)) may be identified. This may allow new relationships between variants to be discovered or types of behavior of similar variants to be predicted. For example, if a first variant is identified with a specified behavior in a first article, and the first variant is linked to a second variant in that article, then the second variant may be predicted to have a similar behavior as the first variant.

At operation 1030, the 'omics data (e.g., DNA, RNA, protein, etc.) may be normalized and associated with a particular genomic variant via an identifier. This representation may allow the variant to be matched to specific cancer-types and/or allow identification of specific drugs predicted to have an optimal therapeutic effect for that variant. In other examples, cohort analysis may be performed, in which individuals having one or more common factors (e.g., age, demographics, variant, etc.) may be grouped together and analyzed, to allow identification of an optimal treatment/drug for that cohort.

Figure 7:
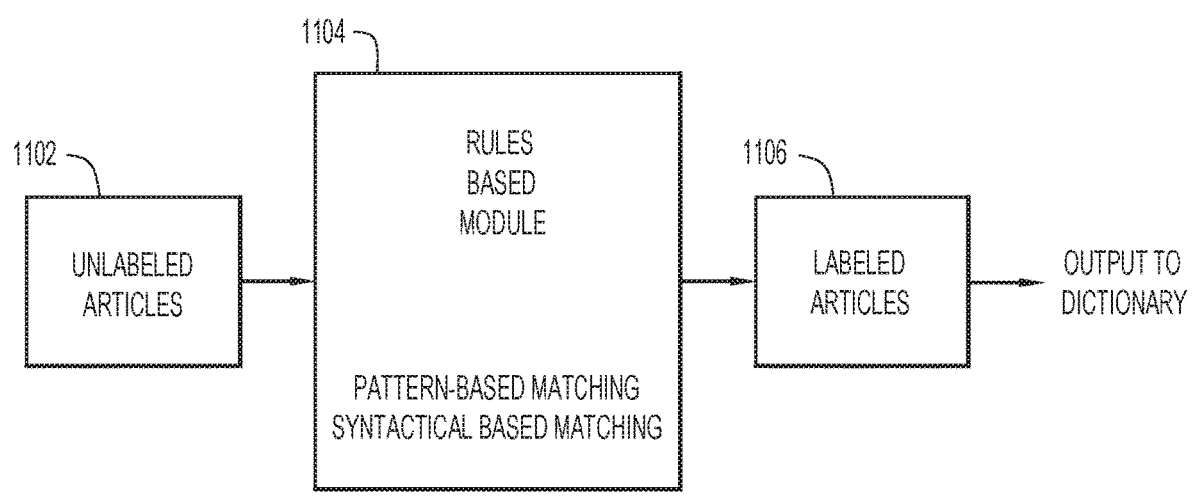
FIG. 7 is an example flowchart showing rule-based operations of the normalization and annotation module, according to embodiments of the present disclosure.

FIG. 7 shows an example flow chart of a rules-based module. Unlabeled articles or documents 1102 may be provided to the rules-based module 1104, which may perform pattern matching, syntactical matching, grammatical or other rules-based techniques to identify gene variants and genes, which may be associated with one another. Once the genes and gene variants have been identified, the articles can be annotated/labeled to generated labeled articles 1106 (e.g., with the ICEID) as containing particular gene variants and genes. In some aspects, this information may be used to generate a dictionary of terms for a specific gene variant.

Figure 8:
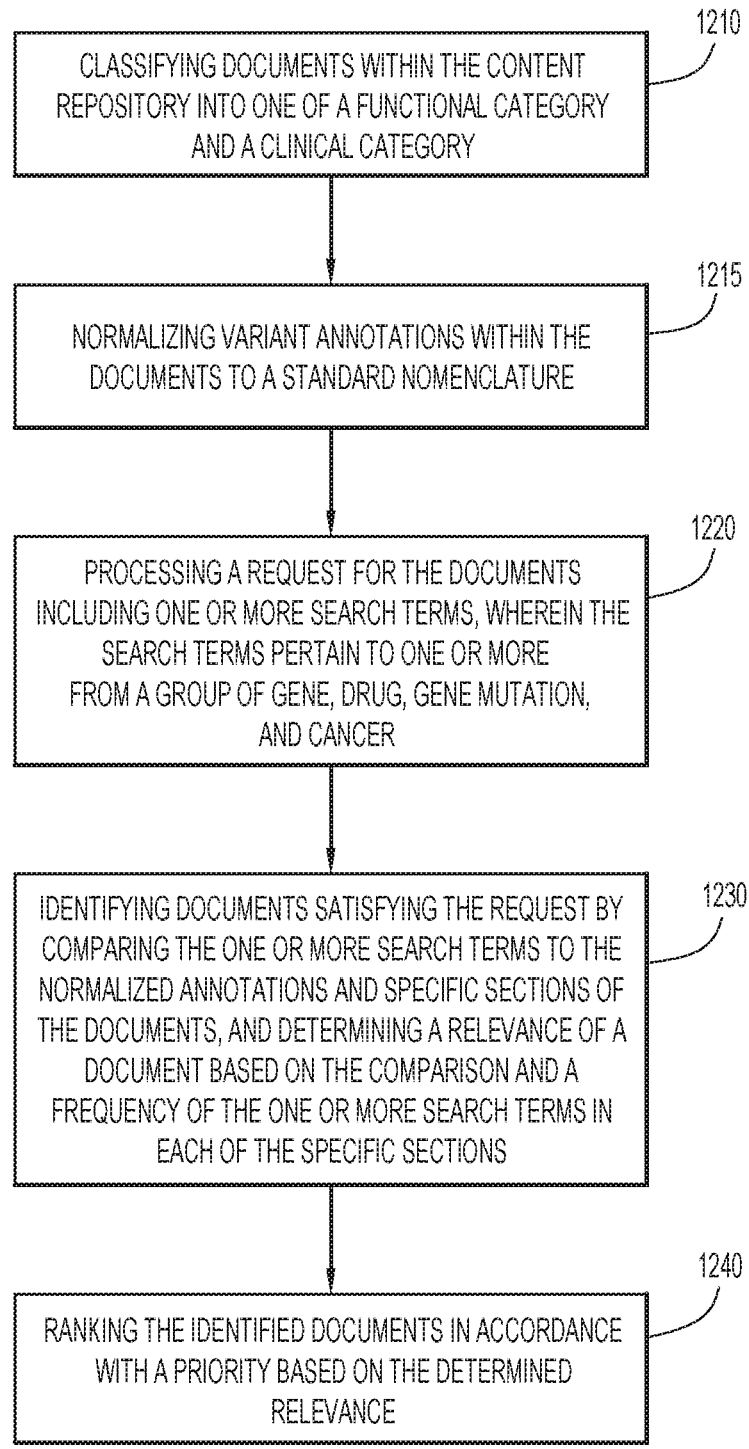
FIG. 8 is a high level flow diagram of the document filtration and normalization and annotation system, according to embodiments of the present disclosure.

FIG. 8 is a flow chart of example operations. At operation 1210, documents may be classified within the content repository into one of a functional category and a clinical category. At operation 1215, variant annotations may be normalized within the documents to a standard nomenclature. At operation 1220, a request is processed for the documents including one or more search terms, where the search terms pertain to one or more from a group of gene, drug, gene mutation, and cancer. At operation 1230, documents satisfying the request are identified by comparing the one or more search terms to the normalized annotations and specific sections of the documents, and determining a relevance of a document based on the comparison and a frequency of the one or more search terms in each of the specific sections. At operation 1240, the identified documents are ranked in accordance with a priority based on the determined relevance.

In one embodiment, variant annotations may be normalized within the documents to a standard nomenclature, and requests for the documents including one or more search terms may be processed. Relevant documents satisfying the request may be identified by comparing the one or more search terms to the normalized annotations and specific sections of the documents, and the results ranked. By normalizing variant annotations through extracting gene variants within a document, and associating each extracted gene variant with a unique identifier corresponding to that gene variant, a standard nomenclature is generated for each variant, allowing identification of the variant across a corpus of documents. In other aspects, a user may search for any of the forms, e.g., present in the corresponding dictionary, to identify the gene or gene variant in the document corpus.

In another embodiment, normalizing the variant may include selecting a form from the group consisting of a DNA sequence, a RNA sequence, an amino acid sequence, or a phrase containing a reference to the variant, as well as other possible forms comprising information pertaining to the gene variant. This approach improves the quality and completeness of the information provided about the gene variant during a search, as more forms of the variant are identified during the search.

Present techniques provide a variety of advantages over existing approaches. For example, custom dictionaries of genes/gene variants may be developed, allowing robust searching capabilities for specific information or combinations of specific information. A customized rules-based module may be used to extract, standardize, and normalize gene annotations from a cancer-specific corpus of information, including full-text articles, to the human genome. This allows a holistic view of the variant across a corpus of information, as different types of information are identified and standardized, and provided in one or more dictionaries.

The present system uses the normalized data to identify novel types of relationships from the cancer-specific corpus (e.g., indels, mutations, copy number variations, chromosomal rearrangements, viral integration into the cancer genome, etc.). Documents may be returned (ranked) based on a custom scoring system. In general, the system may rely on sequence variation data mapped to nucleic acid databases that are supported by peer-reviewed evidence, ensuring that the information returned by the system is of high quality and accuracy.

Additionally, the system may be fully customized to allow the user to choose what type of information to target (e.g., functional documents, clinical documents, etc. in combination with one or more genes, gene variants, targeted drugs and cancer-types, etc. in a ranked and prioritized manner). Thus, the system is fully customizable as the user can choose what type of information to target (e.g., functional or clinical articles in combination with one or more of genes, gene variants, targeted drugs, and cancer-types, etc.). Finally, present techniques rank the relevancy of articles based upon unique criteria.

To obtain different content, a user may change the custom classification terms lists or generate a new custom classification terms list to obtain targeted information. In some aspects, the terminology used for classification may be curated by a subject matter expert in the field and may include gene names/gene variants, gene targeted drugs, and disease and/or cancer-type names. Further, the results may be optionally ranked according to relevancy of documents. By classifying the documents based on a frequency of custom classification terms in a document, relevant and specific content may be delivered to a user. In some aspects, physicians may obtain information matched with specific mutations (e.g., genomic mutations that cause cancer, resistance mutations, etc.) with optimal treatment for those factors to improve patient care.

Present techniques also offer enhanced searching and new capabilities as a user can access particular types of content. In particular, users can access articles comprising gene names, drug names and cancer types that are strictly functional articles or strictly clinical articles. Present techniques may be integrated with precision cancer medicine (also referred to as personalized medicine or genomic medicine). In precision medicine, an individual's genomic profile is determined to identify genetic biomarkers that predict drug response. Types of biomarkers may include: 1) predictive (response to treatment), 2) predictive (drug resistance), 3) predictive (predisposition to cancer), 4) prognostic (biomarkers), or 5) diagnostic (biomarkers). Accordingly, the present system provides a way to search for and access information specific to a particular patient to generate a customized treatment plan. By normalizing variant annotations, a comprehensive analysis of a gene variant across a corpus of data can be performed, allowing information associated with different forms of a variant to be identified and analyzed.

It will be appreciated that the embodiments described above and illustrated in the drawings represent only a few of the many ways of implementing embodiments for filtering and scoring articles using a rules-based approach to access specific, customized information, where the information may be normalized across a corpus of documents, allowing new types of relationships to be discovered.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, document filtration and scoring system, etc.). These systems may include any types of monitors and input devices (e.g., keyboard, mouse, voice recognition, etc.) to enter and/or view information.

It is to be understood that the software (e.g., document filtration and scoring system 15 and document pre-processing module 71, document sectioning module 72, classifier term matching module 73, weighting/classification module 74, drug and gene subset module 75, normalization and annotation module 77, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., document filtration and scoring system 15 and document pre-processing module 71, document sectioning module 72, classifier term matching module 73, weighting/classification module 74, drug and gene subset module 75, normalization and annotation module 77, etc.) may be available on a non-transitory computer usable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., content repository 42, dictionaries 43, classified documents 44, unclassified documents 46, custom classification terms lists 48, metadata 49, etc.). The database system may be implemented by any number of any conventional or other databases, data stores or storage structures (e.g., files, databases, data structures, data or other repositories, etc.) to store information (e.g., content repository 42, dictionaries 43, classified documents 44, unclassified documents 46, custom classification terms lists 48, metadata 49, etc.). The database system may be included within or coupled to the server and/or client systems. The database systems and/or storage structures may be remote from or local to the computer or other processing systems, and may store any desired data (e.g., content repository 42, dictionaries 43, classified documents 44, unclassified documents 46, custom classification terms lists 48, metadata 49, etc.).

The present invention embodiments may employ any number of any type of user interface (e.g., Graphical User Interface (GUI), command-line, prompt, etc.) for obtaining or providing information (e.g., content repository 42, dictionaries 43, classified documents 44, unclassified documents 46, custom classification terms lists 48, metadata 49, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The report may include a listing of prioritized documents along with any other information arranged in any fashion, and may be configurable based on rules or other criteria to provide desired information to a user (e.g., article analytics, weighting scores, search terms, normalized terms, identifiers, etc.).

The present invention embodiments are not limited to the specific tasks or algorithms described above, but may be utilized for any application in which custom filtration and scoring is needed to identify and extract relationships in a content repository, where the content repository contains multiple representations of information pertaining to an entity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises a document of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of managing documents within a content repository comprising:
    classifying documents within the content repository into one of a functional category and a clinical category;
    normalizing variant annotations within the documents to a standard nomenclature wherein a results section of the documents is processed to obtain the normalized annotations, and wherein the results section is identified based on a presence of data generated by an experiment;
    processing a request for the documents including one or more search terms, wherein the search terms pertain to one or more entities from a group of gene, drug, gene variant, and cancer;

identifying documents satisfying the request by comparing the one or more search terms to the normalized annotations and specific sections of the documents, and determining a relevance of a document based on the comparison and a frequency of the one or more search terms in each of the specific sections; and ranking the identified documents in accordance with a priority based on the determined relevance.

2. The method of claim 1, wherein normalizing variant annotations further comprises:

extracting gene variants within a document; and associating each extracted gene variant with a unique identifier corresponding to that gene variant.

3. The method of claim 2, wherein extracting further comprises:

extracting, for each gene variant, a corresponding gene; and associating the gene variant with the corresponding gene.

4. The method of claim 2, wherein extracting further comprises:

identifying multiple forms of the gene variant, wherein the forms are selected from the group consisting of a DNA sequence, a RNA sequence, an amino acid sequence, or a phrase containing a reference to the gene variant.

5. The method of claim 4, further comprising:

annotating, using a rules-based system, unlabeled documents in a corpus to indicate a presence of the gene variant in respective documents.

6. The method of claim 5, further comprising:

generating a dictionary for each gene variant, the dictionary comprising the multiple forms of the gene variant and the corresponding unique identifier for that gene variant.

7. The method of claim 1, wherein the search terms include a gene or gene variant and wherein the specific sections used to rank the documents include the results section of respective documents.

8. The method of claim 1, further comprising identifying new relationships between the entities based on analyzing the normalized variant annotations.

9. A computer system for managing documents within a content repository, wherein the system comprises at least one processor configured to:

classify documents within the content repository into one of a functional category and a clinical category;

normalize variant annotations within the documents to a standard nomenclature, wherein a results section of the documents is processed to obtain the normalized annotations, and wherein the results section is identified based on a presence of data generated by an experiment;

process a request for the documents including one or more search terms, wherein the search terms pertain to one or more entities from a group of gene, drug, gene variant, and cancer;

identify documents satisfying the request by comparing the one or more search terms to the normalized annotations and specific sections of the documents, and determine a relevance of a document based on the comparison and a frequency of the one or more search terms in each of the specific sections; and rank the identified documents in accordance with a priority based on the determined relevance.

10. The system of claim 9, wherein the processor is further configured to:

extract gene variants within a document; and associate each extracted gene variant with a unique identifier corresponding to that gene variant.

11. The system of claim 10, wherein the processor is further configured to:

extract, for each gene variant, a corresponding gene; and associate the gene variant with the corresponding gene.

12. The system of claim 10, wherein the processor is further configured to:

identify multiple forms of the gene variant, wherein the forms are selected from the group consisting of a DNA sequence, a RNA sequence, an amino acid sequence, or a phrase containing a reference to the gene variant.

13. The system of claim 12, wherein the processor is further configured to:

annotate, using a rules-based system, unlabeled documents in a corpus to indicate a presence of the gene variant in respective documents.

14. The system of claim 12, wherein the processor is further configured to:

generate a dictionary for each gene variant, the dictionary comprising the multiple forms of the gene variant and the corresponding unique identifier for that gene variant.

15. The system of claim 9, wherein the search terms include a gene or gene variant and wherein the specific sections used to rank the documents include the results section of respective documents.

16. The system of claim 9, wherein the processor is further configured to identify new relationships between the entities based on analyzing the normalized variant annotations.

17. A computer program product for managing documents within a content repository, the computer program product comprising one or more computer readable storage media collectively having program instructions embodied therewith, the program instructions executable by a computer to cause the computer to:

classify documents within the content repository into one of a functional category and a clinical category;

normalize variant annotations within the documents to a standard nomenclature, wherein a results section of the documents is processed to obtain the normalized annotations, and wherein the results section is identified based on a presence of data generated by an experiment;

process a request for the documents including one or more search terms, wherein the search terms pertain to one or more entities from a group of gene, drug, gene variant, and cancer;

identify documents satisfying the request by comparing the one or more search terms to the normalized annotations and specific sections of the documents, and determine a relevance of a document based on the comparison and a frequency of the one or more search terms in each of the specific sections; and rank the identified documents in accordance with a priority based on the determined relevance.

18. The computer program product of claim 17, wherein the program instructions are executable to:

extract gene variants within a document; and associate each extracted gene variant with a unique identifier corresponding to that gene variant.

19. The computer program product of claim 18, wherein the program instructions are executable to:

extract, for each gene variant, a corresponding gene; and associate the gene variant with the corresponding gene.

20. The computer program product of claim 18, wherein the program instructions are further executable to:
   identify multiple forms of the gene variant, wherein the forms are selected from the group consisting of a DNA sequence, a RNA sequence, an amino acid sequence, or a phrase containing a reference to the gene variant; and
   generate a dictionary for each gene variant, the dictionary comprising the multiple forms of the gene variant and the corresponding unique identifier for that gene variant.

* * * * *